(12) United States Patent  
Scott (10) Patent No.: US 7,081,611 B2  
(45) Date of Patent: Jul. 25, 2006

(54) SELECTIVE WEED DISCRIMINATION

(75) Inventor: Christopher C. Scott, Gingin (AU)

(73) Assignee: Weed Control Australia Ltd., Subiaco (AU)

( * ) Notice: Subject to any disclaimer, the term of this patent is extended or adjusted under 35 U.S.C. 154(b) by 110 days.

(21) Appl. No.: 10/476,105

(22) PCT Filed: Apr. 26, 2002

(86) PCT No.: PCT/AU02/00519

§ 371 (c)(1),  
(2), (4) Date: Mar. 30, 2004

(87) PCT Pub. No.: WO02/088679

PCT Pub. Date: Nov. 7, 2002

(65) Prior Publication Data

US 2004/0149893 A1    Aug. 5, 2004

(30) Foreign Application Priority Data

Apr. 26, 2001 (AU) ..................... PR4574

(51) Int. Cl.  
*A01G 27/00* (2006.01)  
*G01J 1/04* (2006.01)

(52) U.S. Cl. ............ 250/221; 239/155; 41/1.7

(58) Field of Classification Search ........ 250/221, 250/222.1, 226; 356/407, 416, 425; 209/576, 209/577, 579–582; 47/1.7, 1.01; 56/10.1, 56/10.2 R, 10.2 D, 10.2 E, 10.2 G, 10.2 H; 239/146, 155, 159  
See application file for complete search history.

(56) References Cited

U.S. PATENT DOCUMENTS

| 4,015,366 A | 4/1977 | Hall, III |
| 4,347,418 A | 8/1982 | Nobue et al. |
| 4,727,600 A | 2/1988 | Avakian |
| 5,144,767 A | 9/1992 | McCloy et al. |
| 5,222,324 A | 6/1993 | O'Neall et al. |

(Continued)

FOREIGN PATENT DOCUMENTS

| AU | 37775/89 A | 1/1990 |
| DE | 4413739 A1 | 10/1995 |

(Continued)

*Primary Examiner*—Stephone B. Allen  
(74) *Attorney, Agent, or Firm*—M. Henry Heines; Townsend and Townsend and Crew, LLP (57) ABSTRACT

An apparatus (22) for selectively discriminating vegetation or plant matter (28) comprises a light emitting means (24), a light sensing means (30) and a distance sensing means (34). The light emitting means generates a beam of light (26) that can be directed onto plants or plant matter moving relative to the apparatus. The light sensing means senses light transmitted from said light emitting means and reflected from the plants or plant matter, and generates a reflection signal in response to the sensing of the reflected light. The distance sensing means senses the relative distance moved and generates a distance signal. A processing means (32) is operatively connected to the light sensing means and the distance sensing means to combine the reflection signal and distance signal to discriminate different types of plants or plant matter.

24 Claims, 8 Drawing Sheets

U.S. PATENT DOCUMENTS

| | | |
|---|---|---|
| 5,606,821 A | 3/1997 | Sadjadi et al. |
| 5,623,259 A | 4/1997 | Giangardella |
| 5,793,035 A * | 8/1998 | Beck et al. ............... 250/222.1 |
| 5,818,339 A | 10/1998 | Giles et al. |
| 5,842,307 A * | 12/1998 | May ............................. 47/1.7 |
| 6,443,365 B1 | 9/2002 | Tucker et al. |
| 6,584,390 B1 * | 6/2003 | Beck ........................... 701/50 |

FOREIGN PATENT DOCUMENTS

| | | |
|---|---|---|
| DE | 4446481 A1 | 6/1996 |
| JP | 08285765 A | 11/1999 |
| WO | WO 89/12510 A1 | 12/1989 |
| WO | WO 94/02812 A1 | 2/1994 |
| WO | WO 98/21943 A | 5/1998 |
| WO | WO 99/30133 A | 6/1999 |

* cited by examiner

SELECTIVE WEED DISCRIMINATION

FIELD OF THE INVENTION

The present invention relates to a method and apparatus for discriminating different types of ground vegetation in agriculture and relates particularly, but not exclusively, to an agricultural boom spray that incorporates such an apparatus.

BACKGROUND TO THE INVENTION

Over the last couple of decades broad acre spraying has become an essential component of crop management on most farms in Australia. Chemical companies have developed new chemical pesticides for killing weeds, insect pests and diseases which attack cash crops. The most commonly used technique for broad acre spraying of pesticides is the use of boom sprays, which may be self-propelled or towed behind another vehicle. A typical boom spray has a plurality of spray nozzles mounted at spaced locations along a boom, a large tank for containing the spray liquid and a pump system for pumping the liquid to the nozzles. A control system is usually provided for controlling the rate at which the pesticide is sprayed relative to ground speed, and a marker system may be used to aid driving and avoid overlapping.

One of the disadvantages of conventional boom sprays is that herbicides are sprayed indiscriminately on the crop, bare ground and weeds. This is of concern in the case of food crops, with consumer groups becoming increasingly vocal about chemical residue in crops and livestock. There is also an economic disincentive since a much greater volume of chemical spray must be applied per hectare than is actually required to effectively control the weeds.

Co-pending Australian patent application No. 16482/99 describes a method and device for discriminating different types of ground vegetation in agriculture in which an artificial light source is employed for directing a beam of light onto the vegetation. A sensor assembly is provided for detecting reflected radiation from the vegetation in a selected wavelength band and generating a sensing signal in response to the detection. A logic controller determines whether a magnitude of the sensing signal falls within a predetermined range of values in order to distinguish one type of vegetation from another type. In the red and near infrared wavelengths there is some variation in reflectance from one plant to another, depending on a number of factors. The logic controller compares the amplitude of the sensing signal with a decision window. If the amplitude of the incoming sensing signal falls within the decision window then the logic controller determines that a certain type of plant has been detected and activates the corresponding solenoid valve to deliver a dose of spray liquid from a spray nozzle to the targeted weed.

With certain types of vegetation, it is not possible to distinguish weed from crop plants based on the sensing of the reflected radiation alone. Therefore, AU 16482/99 also describes the use of a plurality of sensors arranged in an array with a geometric configuration adapted to aid in discriminating different types of vegetation. For example, a linear array of three sensors can be adapted to distinguish a stem type target vegetation such as, for example, skeleton weed (*Chondrilla juncea* L.). A unique decision window for each sensor in the array is programmed into the logic controller in order to detect sensing signals which fall within respective decision windows. By a judicious choice of geometric array of sensors and providing a unique decision window for each sensor, the logic controller can accurately distinguish between different shaped plants.

Whilst the above arrangement of sensors in a geometric array works very well, in practice the need to change the geometric array for each type of weed desired to be distinguished is rather inconvenient.

SUMMARY OF THE PRESENT INVENTION

The present invention was developed with a view to providing a more efficient method and apparatus for discriminating different types of ground vegetation in agriculture, without the need to change hardware components of the apparatus every time a different type of plant is to be discriminated. Although the invention will be described primarily with reference to the selective spot spraying of weeds, it will be apparent that the method and apparatus for discriminating different types of ground vegetation may also be used to identify weeds for mechanical destruction, mapping of weed infestation coupled with a global positioning system (GPS) or differential global positioning system (dGPS), differentiated spraying of liquid fertiliser on crop plants, measurement and logging of crop vigour, and other weed and crop management practices. It will also be apparent that the invention is not limited in its application to broadacre farming but may also, for example, be applied to intensive row crop farming, or identification for sorting of plant matter such as fruit or other produce Throughout this specification the term "comprising" is used inclusively, in the sense that there may be other features and/or steps included in the invention not expressly defined or comprehended in the features or steps subsequently defined or described. What such other features and/or steps may include will be apparent from the specification read as a whole.

Throughout this specification the term "light" is to be understood to include electromagnetic radiation in the visible as well as the invisible spectrum, and thus includes, for example, radiation in the infra-red as well as the near infra-red regions.

According to one aspect of the present invention there is provided an apparatus for selectively discriminating vegetation or plant matter, the apparatus comprising:

light emitting means for generating a beam of light that can be directed onto plants or plant matter over which the light emitting means moves relative to the plants or plant matter;

light sensing means for sensing light transmitted from said light emitting means and reflected from said plants or plant matter, and generating a reflection signal in response to said sensing;

distance sensing means for sensing the relative distance moved in relation to said plants or plant matter by said light emitting means and generating a distance signal in response to said sensing; and, processing means operatively connected to said light sensing means and distance sensing means for combining said reflection signal and distance signal whereby, in use, different types of plants or plant matter, including weeds, can be discriminated.

Preferably the processing means combines the reflection signal and distance signal to determine the size and/or shape of the plant or plant matter.

Preferably said distance sensing means includes a wheel encoder for sensing the speed at which a vehicle on which the apparatus is mounted is moving over the ground. Typically said wheel encoder generates a signal in the form of a train of pulses or pulse count, wherein the frequency of the pulses is directly proportional to the speed at which the vehicle moves over the ground, as well as the distance it has travelled. Preferably a separate wheel encoder is provided on each side of the vehicle, so that the processing means is able to identify the distance the vehicle has travelled, when the vehicle is turning, as well as the speed at which it is turning, and adjust the response accordingly.

In one embodiment said light emitting means comprises a plurality of artificial light sources, each light source being adapted to transmit a beam of light at different wavelengths, whereby, in use, the reflection signal at each wavelength is used by the processing means in combination with the distance signal to discriminate plants or plant matter.

Preferably the processing means is programmed to combine the reflection signal and distance signal to discriminate one type of plant matter from another type of plant matter and/or one type of plant matter from non plant matter.

Preferably said light sensing means comprises a plurality of sensor assemblies mounted in an array. Preferably each sensor assembly comprises a pair of sensors mounted in close proximity and each adapted to detect the reflected light at different wavelengths. Typically the sensors employed are photodiodes. Preferably a first sensor in each assembly is adapted to generate a sensing signal when it detects reflected light having a wavelength peaking between 550 nm and 650 nm. Preferably a second sensor in each assembly is adapted to generate a sensing signal when it detects reflected light having a wavelength peaking between 850 nm and 950 nm.

Preferably each sensor assembly includes one or more further sensors adapted to generate a sensing signal when each further sensor detects reflected light having a predetermined wavelength in the visible, near infra-red or infra-red wavelength bands, wherein the processing means is operatively connected to the further sensors, wherein the sensing signals from the further sensors are used to discriminate plants or plant matter.

Preferably the first and second sensors are mounted concentrically in order to reduce the incidence of "false positive" spectral responses, in that if the second sensor reads reflected light from a target, that same target must also have passed under the first sensor.

Preferably the further sensors are mounted concentrically with the first and second sensors.

Preferably the processing means is configured to produce an output signal when a target plant is identified or when an object that is not the target plant is identified. Preferably the apparatus includes a response means arranged to provide a response to the output signal. Preferably the response means is one or more of: a solenoid valve arranged to operate a means for spraying the target plant or object; a valve means arranged to operate a means for distributing a powder or particulate material; a recording means for recording the presence (or absence) and location of the target plant or object; a cutting means for cutting material in response to identification of the target plant or object; or a cultivating means, such as an actuator for a hoe.

According to another aspect of the present invention there is provided a method for selectively discriminating vegetation or plant matter, the method comprising the steps of:

generating a beam of light that can be directed onto plants or plant matter over which the light emitting means moves relative to the plant or plant matter;

sensing light transmitted from said light emitting means and reflected from said plants or plant matter, and generating a reflection signal in response to said sensing;

sensing the distance moved relative to said plants or plant matter by said light emitting means and generating a distance signal in response to said sensing; and, processing said reflection signal and distance signal to determine the spectral characteristics and size and/or shape of the plants or plant matter whereby, in use, different types of plants or plant matter, including weeds, can be discriminated.

Preferably the light is sensed by one or more sensor assemblies having one or more sensors. Preferably as the sensor assemblies travel over the ground each of the sensors in the sensor assemblies continually senses light reflected upwards from the ground surface. Alternatively the plants or plant matter travel underneath stationary sensor assemblies, wherein each of the sensors in the sensor assemblies continually senses light reflected from the plants or plant matter.

However, preferably when a first affirmative spectral response occurs, the processing means begins to "strobe" the sensor assemblies so that they only operate to sense the presence or absence of the target plant matter at discretely spaced intervals.

Preferably readings from each of a plurality of sensor assemblies used for sensing the reflected light are taken at uniformly spaced intervals over the ground surface, and are typically triggered by pulses generated via a wheel encoder used for sensing the distance travelled over the plants. Typically the interval spacing is set at a fixed distance, typically between 0.2 mm and 2 mm when travelling in a straight line.

DETAILED DESCRIPTION OF PREFERRED EMBODIMENTS

In order to facilitate a more detailed understanding of the nature of the invention a preferred embodiment of an apparatus and method for discriminating different types of ground vegetation will now be described in detail, by way of example only, with reference to the accompanying drawings, in which:

FIGS. 1(a) and (b) illustrate a boom spray which incorporates an apparatus for discriminating different types of ground vegetation in accordance with the present invention;

FIGS. 1(a) and (b) illustrate a typical agricultural spraying apparatus known as a boom spray, in this case of the kind that is towed behind another vehicle, tractor 10. The boom spray is in the form of a trailer on which is mounted a large tank 12 for containing the spray liquid, typically a herbicide or other chemical pesticide. A pump system (comprising pump, tank, pipework and valves etc, not shown) pumps the spray liquid to a plurality of nozzles 14 mounted at spaced locations along a transversely mounted boom 16. A spray liquid supply line 18 which extends the full length of the boom supplies the herbicide to each of the spray nozzles 14. An apparatus 22 for discriminating different types of ground vegetation is mounted on the boom spray and controls the delivery of spray liquid from the nozzles 14 depending on the type of vegetation distinguished by the apparatus 22.

Figure 2A:
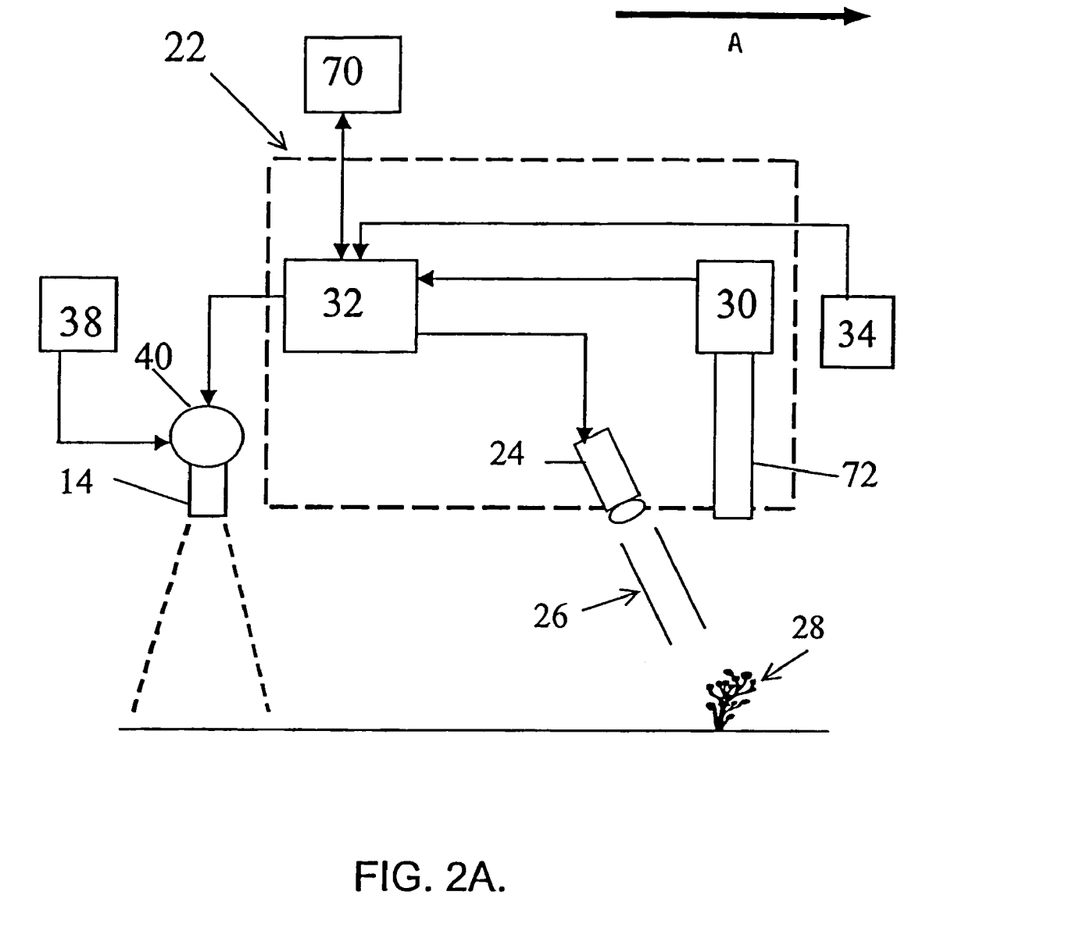
FIGS. 2A and 2B are schematic illustrations of a preferred embodiment of the apparatus for discriminating different types of ground vegetation employed in the boom spray of FIG. 1.

One embodiment of the apparatus 22 for discriminating different types of ground vegetation is illustrated schematically in FIG. 2A. The device 22 comprises an artificial light emitting means 24 for directing a beam 26 of light onto the vegetation 28. In this embodiment, the light emitting means 24 is a pair of light emitting diodes (LEDs) and associated lensing that emit light at a wavelength of 635 nm and 875 nm respectively. However any suitable artificial light emitting means may be employed such as a wide-spectrum quartz halogen lamp or a laser. The use of LEDs is particularly advantageous as it enables light beams to be generated at the particular wavelengths of interest with low power consumption. In this connection, one or more LEDs adapted to emit light at selected wavelengths may be employed for light emitting means 24. A sensor assembly 30 for detecting light from the LEDs 24 reflected from the vegetation 28 in a selected frequency band is also provided, and typically includes a lens system for focusing on the vegetation. One or more filters may be employed to permit light in selected frequency bands to pass through to the sensor assembly 30. Sensors in the sensor assembly 30 generate a sensing signal in response to detection of the reflected light.

The apparatus 22 also includes a processing means, in this case in the form of a microprocessor-based controller 32 for determining whether a magnitude of the sensing signal from the sensor assembly 30 falls within a predetermined range of values. The predetermined range of values or decision window is programmed into the controller 32 so that it is able to distinguish one type of vegetation from another type based on the magnitude of the sensing signal from the sensor assembly 30.

The apparatus 22 further comprises a distance sensing means, which in this embodiment includes a wheel encoder 34 for sensing the speed at which the trailer on which the apparatus 22 is mounted is moving over the ground. Wheel encoder 34 is operatively connected to the controller 32 and generates a signal in the form of a train of pulses or pulse count. The frequency of the pulses is directly proportional to the speed at which the trailer moves over the ground, and provides information regarding the distance it has travelled. Controller 32 is able to calculate the actual distance travelled based on the diameter of the trailer wheels 36. Wheel encoder 34 detects the speed at which a wheel 36 of the trailer on which the apparatus 22 is mounted moves. Any suitable type of wheel encoder may be employed.

For example, one form of wheel encoder comprises a shaft geared to the wheel axle and is adapted to generate 2000 encoder pulses per revolution. In the described embodiment, a flywheel gear is provided on the wheel axle adjacent one of the wheels 36 on both sides of the trailer. A sensor is mounted adjacent the rim of the flywheel and is adapted to generate a pulse every time it detects one of the teeth on the flywheel rim. The train of digital pulses or pulse count thus generated is received by the controller 32 to calculate the distance travelled by the trailer, and hence by the sensor assembly 30 as it travels over the ground. Preferably a separate wheel encoder is provided on each side of the trailer, so that the controller 32 is able to identify when the trailer is turning, as well as the speed at which it is turning, and adjust the response time along the length of the boom accordingly. This data is processed by controller 32 to provide compensation for turning and this compensation ensures that like plant species are similarly identified irrespective of curvature of travel. Although the use of two wheel encoders is the preferred arrangement, the system will still function with one wheel encoder only.

Figure 2B:
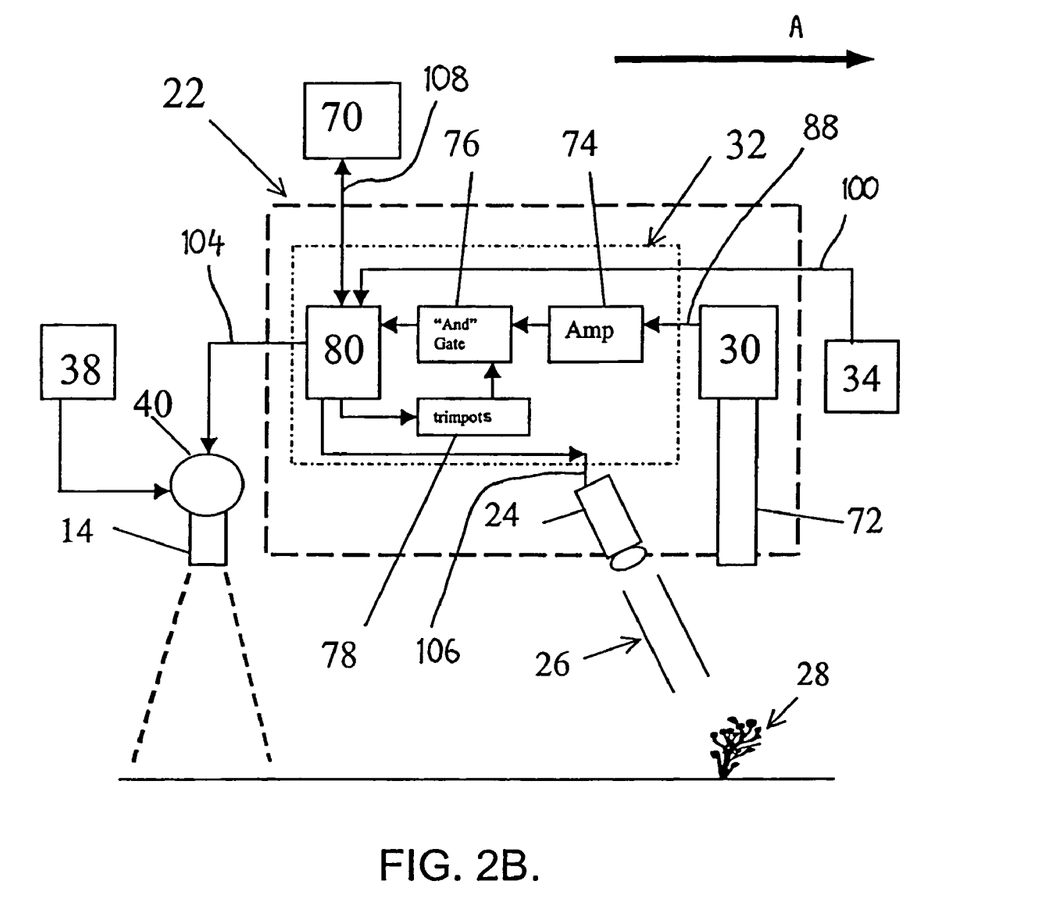

FIG. 2B shows the apparatus 22 including the controller 32 in more detail. Controller 32 includes an amplifier means 74, an "AND gate" means 76, trimpots 78 and a microprocessor 80. Signals from sensor assembly 30 are provided to the amplifier means 74 by connection 88. The signals are boosted by the amplifier means 74 and then provided to the AND gate means 76. The trimpots 78 provide adjustable minimum and maximum reference levels to the AND gate means 76. The reference levels are used to trigger the AND gate means 76 when the input signal from the amplifier means 74 falls within the minimum and maximum reference levels. The reference levels are set according to the desired level of reflectance received by the sensor assembly 30 to indicate the presence of selected vegetation as will be described in more detail below. The range of values between the minimum and maximum reference levels set in each trimpot are referred to as the "decision window" in the description below. Triggering of the AND gate means 76 indicates to the microprocessor 80 that the required level of reflectance has been detected by the sensor array 30. Input signals from the wheel encoder 34 are transmitted by connection 100 to the microprocessor 80. Outputs 104 and 106 from the microprocessor will be described in more detail below, as will input/output 108.

By combining the reflection signal information received from the sensor assembly 30 with the distance information provided by the wheel encoder 34, controller 32 is able to determine the plant matter characteristics, such as leaf characteristics. Plant matter characteristics include the spectral response and size and/or shape of the leaves, fruit or plant parts of the ground vegetation. Determining the plant matter characteristics enables discrimination between different types of plants as the apparatus travels over the ground. The method by which it does this will be described in more detail below with reference to FIGS. 3, 4 and 5.

A pump and chemical supply system 38 is provided with a plurality of high speed solenoid controlled valves 40 for controlling the delivery of spray liquid from each nozzle 14. The solenoid controlled valves 40 are also under the control of microprocessor-based controller 32, via connection 104. Hence, when the controller 32 detects the presence of, for example, a weed on the basis of the combination of the sensing signal information generated by the sensor assembly 30 and the distance pulses generated by the wheel encoder 34, it activates the solenoid controlled valve 40 to release a jet of spray liquid from the nozzle 14 onto the weed.

Figure 1:
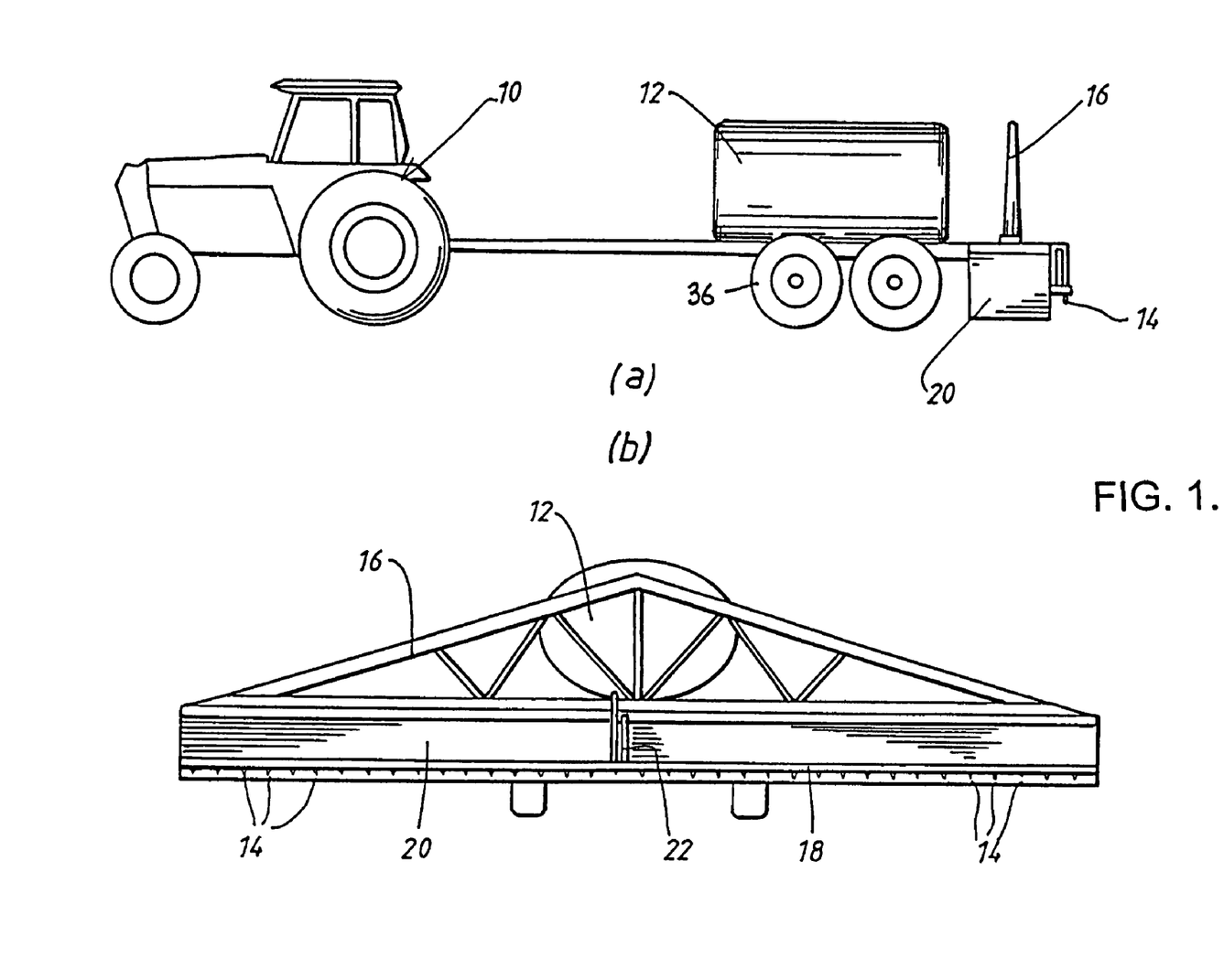

Preferably a shroud 20 is suspended from the boom 16 as shown in FIG. 1, in order to minimise the amount of sunlight which might reach the sensors and interfere with the detection of reflected radiation. Shroud 20 is made from a flexible, light-impervious material and is of sufficient length to shade any vegetation directly below the LEDs 24 and sensor assembly 30 from direct sunlight throughout most of the day. If the apparatus is operated after dark, the shroud 20 may be dispensed with.

Preferably the boom 16 is designed to travel at a fairly constant height as it moves over the ground, so as to minimise variations in the intensity of the reflected light due to changes in the distance of the light source 24 and the sensor assembly 30 from the ground vegetation. Preferably, the sensor assembly is maintained at a height of between 10 mm to 1000 mm above the target vegetation, more preferably between 200 mm to 800 mm above the target vegetation. Although it has been found that the magnitude of the sensing signal does vary with changes in height, these variations are smaller than the difference in magnitude produced by the absorption of electromagnetic radiation by different types of vegetation in selected frequency bands.

Only one light source 24 and sensor assembly 30 are shown in FIG. 2A. However, typically a plurality of sets of light sources and sensor assemblies are provided on the boom spray, located at a distance forward (relative to the direction of travel of the boom) of the spray nozzles 14. One or more sets of light sources and sensor assemblies are used to control a respective spray nozzle 14 in order to discriminate the type of vegetation in the target area of each spray nozzle 14.

Preferably, each sensor assembly 30 comprises a pair of sensors mounted in close proximity and each adapted to detect the reflected light at different wavelengths. Preferably, the sensors employed are photodiodes. A first sensor 44 is adapted to generate a sensing signal when it detects reflected light having a wavelength peaking between 550 nm and 650 nm. Preferably, the second sensor 46 is adapted to generate a sensing signal when it detects reflected light having a wavelength peaking between 850 nm and 950 nm.

Figure 5:
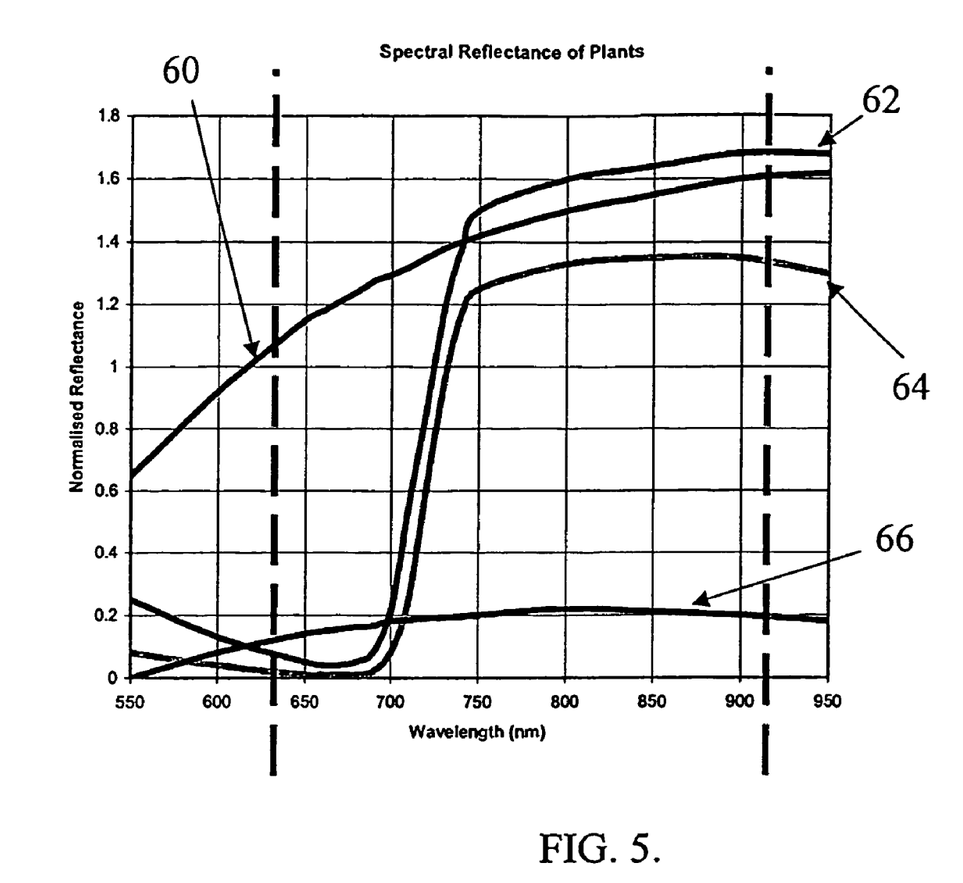
FIG. 5 illustrates graphically the spectral reflectance of various types of plants.
Figure 6A:
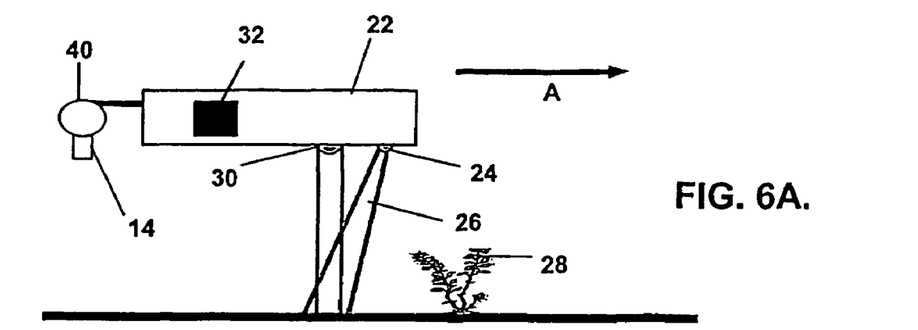
FIG. 6 illustrates the operation of a selective spraying apparatus incorporating a preferred embodiment of the apparatus for discriminating different types of ground vegetation.
Figure 6B:
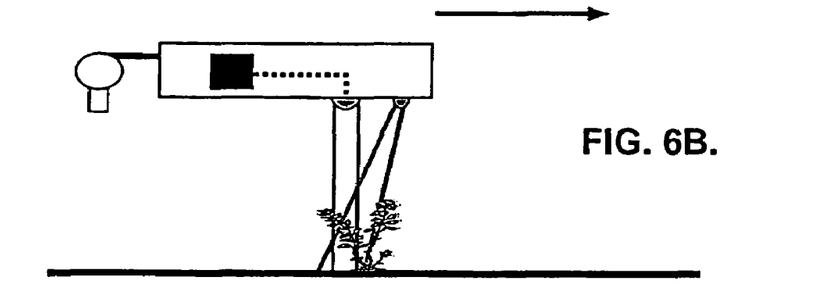
Figure 6C:
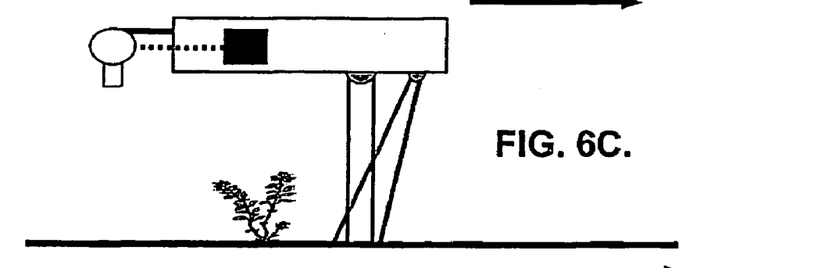
Figure 6D:
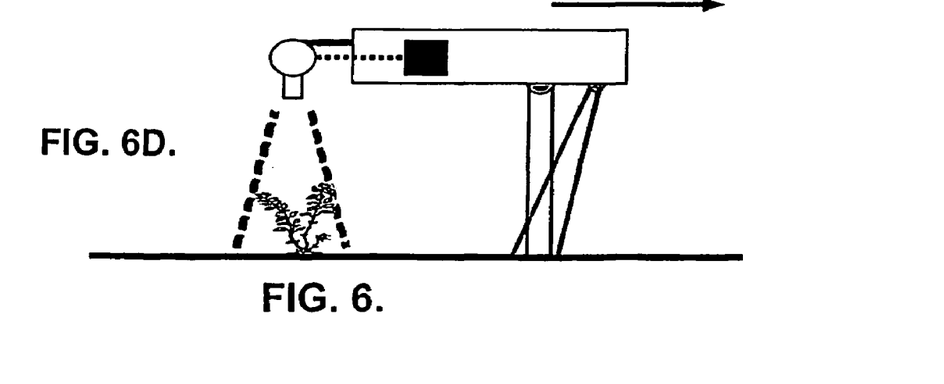

A series of experimental measurements were made to determine the spectral reflectance of various plants. The results in the form of the normalised reflectance measurements plotted against wavelength measurements in nanometres are illustrated in FIG. 5. It was found that with virtually all green leafed plants, the reflectance rises sharply at approximately 700 nm, whereas below this wavelength, very little light is reflected from the plant matter (represented by lines 62 and 64 in FIG. 5). On the other hand, dry, brown plant matter, such as stubble (in side view) continues to have a relatively strong reflectance below 700 nm, as represented by the line marked 60. Above 700 nm, the stubble has a similar reflectance characteristic to that of the green leaf plants. Stubble in end view has a characteristic indicated by 66.

Therefore, by using two sensors, a first sensor 44 for detecting the reflected light at approximately 630 nm and a second sensor 46 for detecting the reflected light at approximately 920 nm (represented by the dotted lines in FIG. 5), it is possible to distinguish between the brown stubble and green leaf plant matter. Namely, if a high sensing signal is generated by both sensors 44 and 46, it indicates that the vegetation is probably stubble, whereas if a high sensing signal is being generated by the second sensor 46, and a low or zero sensing signal is being generated by first sensor 44, it indicates that a green leaf plant has been detected, hereafter referred to as an affirmative spectral response. Controller 32 applies the appropriate logic in order to discriminate between different types of plant matter.

FIG. 5 also illustrates how the magnitude of the sensing signal generated by the second sensor 46 may be used to discriminate between different types of green vegetation. By selecting the appropriate upper and lower limits of each decision window, the controller 32 can in certain circumstances distinguish between different types of green vegetation. At 920 nm, the reflectance characteristic 62 for typical green leaf plant No. 1 has a normalised reflection value falling between 1.6 and 1.8, whereas the reflectance characteristic 64 of the typical green leaf plant No. 2 has a normalised reflectance value falling between 1.2 and 1.4. However, with some vegetation it is not possible to distinguish between the different plants based on the sensing signal generated by the reflected light alone, as the spectral reflectance characteristic is practically indistinguishable. For this reason, the apparatus 22 is also capable of distinguishing the size and/or shape of the plant material. The preferred method of detecting the shape and/or size of the plant material will now be described with reference to FIG. 3.

Figure 3:
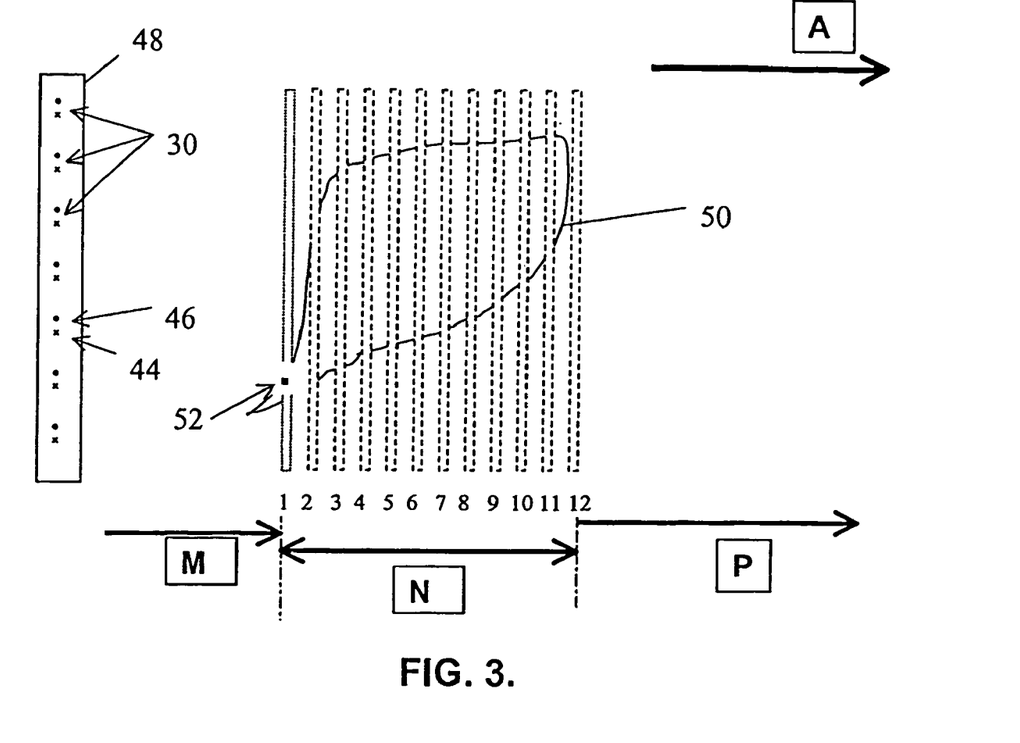
FIG. 3 illustrates schematically the method for discriminating different types of ground vegetation in accordance with a preferred embodiment of the invention.

A plurality of sensor assemblies 30 are shown arranged in a linear array in FIG. 3. As the apparatus travels over the ground in the direction of travel as indicated by arrow A it passes over a plant leaf 50 near the ground. Each of the rectangular strips shown in broken outline in FIG. 3 represents a discrete position of the sensor array as it travels above the ground surface. Preferably, as the sensor array travels over the ground each pair of sensors 44, 46 in the sensor assemblies 30 continually senses light reflected upwards from the ground surface, over the ground section M. Location 52 represents the position at which one of the sensor assemblies first detects the presence of target vegetation and generates an affirmative spectral response. When this first affirmative spectral response occurs, controller 32 changes the illumination to "strobe" the light emitting means 24 and/or discretely samples the sensor assemblies 30 so that it only operates to sense the presence or absence of the target plant matter at discretely spaced intervals, in this case at positions 1 to 12 of the sensor array 48, ie, over ground section N.

At pulse position 12, none of the sensors generate an affirmative spectral response, and thus the pulsing ceases, and the system reverts to a continuous sensing mode, over ground section P. In this embodiment the most efficient operation of the electronics is achieved by the strobing being in operation only when an affirmative spectral response is recorded (ie, ground section N), and reverts to continuous mode at other times. However the system can be fully effective even if the strobing were to operate at all times.

Preferably, readings from each of the sensor assemblies 30 are taken at uniformly spaced intervals over the ground surface, and may be triggered, for example, by the pulses generated via the wheel encoder 34. The interval spacing is set at a fixed setting, typically between 0.2 mm and 2 mm when travelling in a straight line, and when travelling on a curve varies according to the turning circle. Controller 32 is then able to combine the information obtained from the sensing signal generated by the sensors 44 and 46, together with the distance travelled between each reading of the sensors to determine the width of the plant leaf 50 in the direction of travel. If desired, controller 32 can also combine the signals received from adjacent sensor assemblies 30 in order to determine the approximate size and shape of the plant leaf 50.

Figure 4:
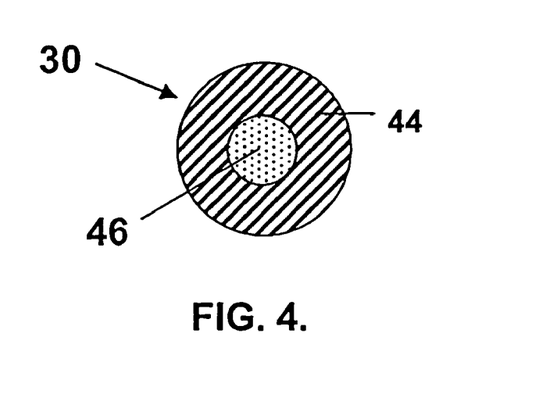
FIG. 4 illustrates a preferred embodiment of a pair of sensors employed in the apparatus of the present invention.

Preferably the first and second sensors 44 and 46 are provided in close proximity, typically immediately adjacent each other as shown in FIG. 3. In order to obtain an affirmative spectral response the signal output from the first sensor 44 (550 nm to 650 nm) must be reading low and the signal output from the second sensor 46 (850 nm to 950 nm) must be reading high at the same time. However, if the first and second sensors 44 and 46 are positioned side by side as shown in FIG. 3, it is possible for example for the apparatus when passing over a piece of stubble lying at an oblique angle to the direction of travel A to record a high reading on the second sensor, and positioned so that it is not under the first sensor, but by the time it passes under the first sensor it has gone past the second sensor. There is a possibility in this sensor configuration for a thin plant such as stubble being read by the two sensors sequentially rather than simultaneously. Hence, there is a brief moment when the first sensor would read low, and the second sensor would be reading high. This is the condition for an affirmative spectral response, however the reading obtained is in fact a "false positive". However, if the first and second sensors 44 and 46 are mounted concentrically as shown in FIG. 4, it is possible to reduce the incidence of "false positives" because both sensors must read the target simultaneously. For a green leaf to achieve an affirmative spectral response with the concentric sensors it first needs to cross the first sensor 44 before it reads high on the inner second sensor 46. If a piece of stubble were to cross the concentric sensor arrangement, it would read high on both sensors 44 and 46, which would not constitute an affirmative spectral response.

A suitable arrangement of lenses and/or filters 72 may be employed in connection with either one or both of the light sources 24 and the sensor assembly 30 in order to better focus the light beam 26 and/or the reflected light onto the sensors in the sensor assembly. Thus, each sensor will preferably have a narrow field of view. Several different arrangements are described in AU16482/99 and will not be described again here.

FIG. 6 illustrates the preferred method of operation of the apparatus for distinguishing different types of ground vegetation in its application to precision spot spraying of weeds. FIG. 6 illustrates the sequence of operation in four steps moving down the page as the apparatus moves over the plant 28 in the direction of travel of the boom spray. In FIG. 6A, the sensor-head approaches the plant 28 and as the sensor assemblies 30 continuously scan the ground the controller 32 records the ground reading and under "non-strike" conditions the spray nozzle 14 remains closed. In FIG. 6B, the sensor assemblies 30 are directly over the plant 28. Controller 32 processes and interprets the information received from the sensor assemblies 30 and the wheel encoder 34 for colour, shape and size of the plant leaf. If controller 32 recognises the characteristics for a target, such as a weed, the controllers 32 registers that the target is detected, hereafter referred to as a "strike". It is noted that the controller 32 may be programmed to register "strikes" for a plurality of targets. At FIG. 6C, if a strike has been registered, the controller sends a signal to the solenoid control valve for the spray nozzle 14. At FIG. 6D, the control of the opening and closing of spray nozzle 14 is determined by controller 32 using information received from the wheel encoder 34, so that only that particular plant 28 is sprayed.

Figure 7:
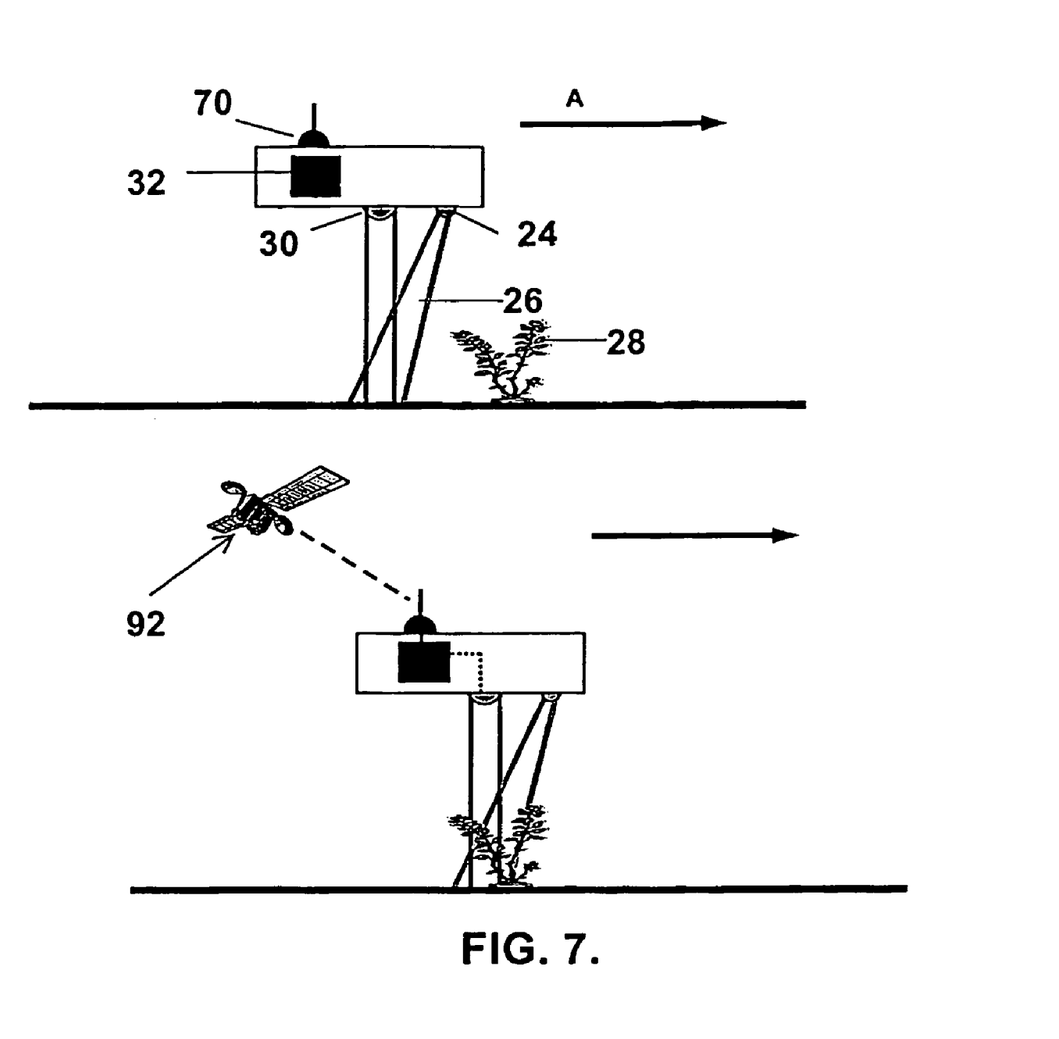
FIG. 7 illustrates the use of dGPS to record the location of a selected type of vegetation; and, FIG. 8 illustrates in more detail a processing means of the apparatus in FIG. 2C.

The controller 32 may be connected by connection 108 to a differential global positioning system (dGPS) 70. Referring to FIG. 7, as the apparatus 22 passes over a selected plant the position of the plant can be recorded by the dGPS 70. A signal received from global positioning system satellites 92 can provide location information to the apparatus 22 so that the position of the plant can then be recorded for later spraying or for monitoring purposes.

Figure 8:
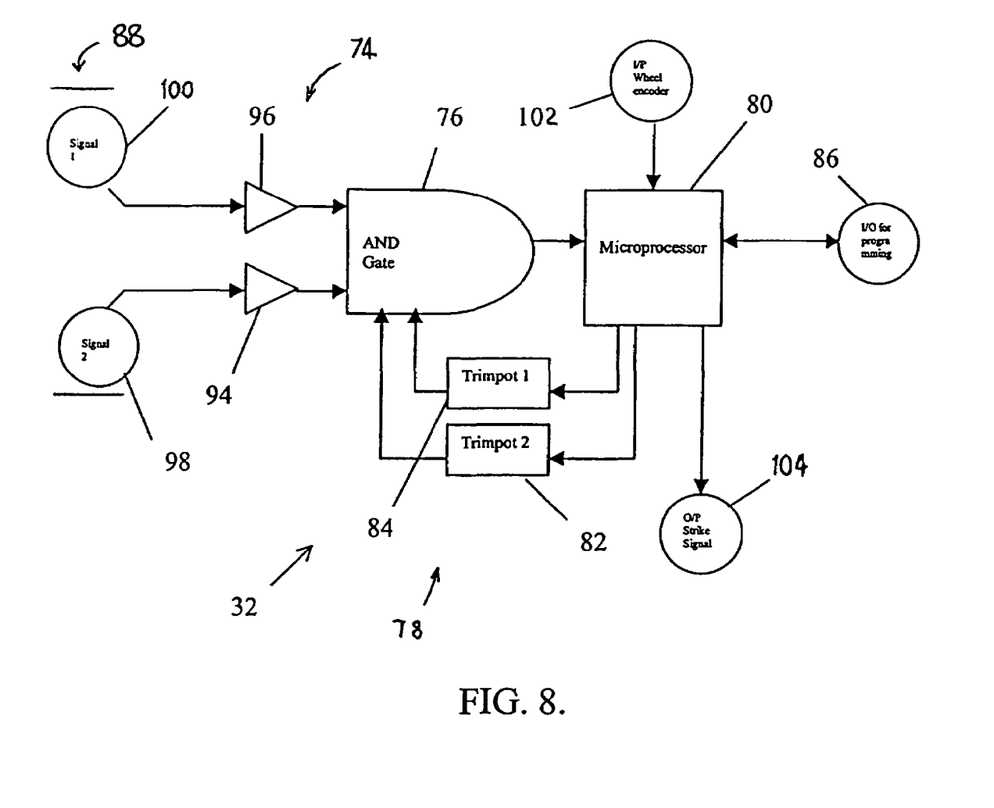

Referring to FIG. 8, controller 32 is described in more detail. The controller includes a printed circuit board on which are mounted amplifier means 74 AND gate means circuitry 76, trimpots 78 and microprocessor 80. When an optical sensor 30 receives light reflected from vegetation the output voltage from each of the sensors 30 is received by connection 88. First signal 100 is received from the first sensor 44, second signal 98 is received from the second sensor 46. Signal 1 and signal 2 are amplified by amplifiers 96 and 94 respectively. Outputs of the amplifiers 96 and 94 are received by the AND gate 76.

A predetermined range of values for a decision window is programmed into the microprocessor 80. From these values, the microprocessor sets digital trimpots 82 and 84 to the upper and lower values of the decision window for each respectively.

If the value of the amplified signal 100 falls within the decision window set in trimpot one 84, and if the value of the amplified signal 98 falls within the decision window set in trimpot two 82, the spectral reflectance criteria have been met to constitute an affirmative spectral response. The input signal 102 from the wheel encoder provides the microprocessor 80 with information to determine leaf size and therefore discriminate vegetation being sensed. A "strike" will be registered only if both the spectral criteria and leaf criteria have been met.

Software for controlling the microprocessor 80 may be downloaded by an external connection 86. Once the microprocessor is programmed the software is stored in storage means, such as FlashRAM or EEPROM within or connected to the microprocessor. Other suitable storage means can also be employed such as a hard disk drive.

Depending on the programming the output signal is then sent to an output device by connection 104, which may be for example a storage system for storing the location from the dGPS 70 and/or a control signal to open the solenoid valves 40. In the case of the microprocessor being programmed to open or close the spray valves 40, it may be programmed to open a selected distance before the target plant and close off a selected distance after the target plant. This can be desirable to ensure the weed is sprayed when travelling at high speeds to ensure there is sufficient over-spray as required by some chemical treatments of weeds. In the case of liquid fertilisers it may be desirable to spray the ground in the proximity of the plant as well as the plant itself. Additionally it is possible to select the output operation within the software to spray fertiliser on cash crop plants, but not on weeds.

In summary the logic contained within the programming can effect many practical applications in agriculture including:

1. Select a Single Species Only

This is applied in a situation where it is the objective to reduce the incidence rate of a problem weed species, or to utilise specific herbicides on problem weed species, or to apply a liquid to one species, or to log the location of those plants 2. Select the Cash Crop Only This can be used to apply fertilisers or pesticides to crops only.

3. Select a Group of Weed Species

This would be applied in a situation where it is the objective to reduce the incidence rate of a number of problem weed species, such as where the objective is to treat multiple weed species, or where a group of specific weeds develop tolerance to broad-spectrum herbicides.

4. Select all Weeds With the Exception of the Crop

This is applied for selectively spraying of weeds-only without substantially over-spraying either the crop or the ground, or for mechanical destruction of weeds-only. This is useful for precision weed management in most types of agricultural crops including pasture.

5. Measure Crop Vigour

In this application, the size and/or spectral response of plant leaves can be logged as an indicator of plant vigour across a paddock. Discolouration or stunted or malformed growth may indicate disease or other growth impediments, which can be identified.

6. Produce Row Cropping Data

The size of plant growth within crop rows can be measured and logged.

7. Discrimination of Fruit/Vegetables

It is possible to discriminate plant matter aside from individual leaves, such as fruit/vegetables, by their size/shape and spectral response. The size, shape and/or colour (spectral response) of fruit and/or vegetables can be measured and logged. This can be useful to determine, say, whether a crop is ripe and ready for harvesting or for identification in sorting after picking. In this example the sensor assembly may be stationary and the plant matter may be moving on a conveyor. The distance sensing means would sense the distance moved by the conveyor.

8. Discrimination of Foreign Objects

It is possible to discriminate non plant matter from plant matter of a plant by the size/shape of the target and the spectral response. Foreign objects could include insects of sufficient size. Other foreign objects may include rubbish or debris blown onto a crop. Foreign objects identified as, say, an insect could be sprayed with an insecticide.

9. Other Applications

Because of the flexibility of the system there are other uses for the technology, namely in the remote sensing of noxious weeds (e.g. skeleton weed) or as a research tool for determining the distribution of weeds to crop ratio or to measure the overall stress levels of plants in general.

Now that a preferred embodiment of the apparatus and method for distinguishing different types of ground vegetation have been described in detail, it will be apparent that the apparatus and method provide significant advantages over the prior art, including the following:

(a) distinguishing of different types of ground vegetation can be effected more accurately;

(b) different types of ground vegetation can be detected by software controlled modifications of the sensing logic employed in the controller, rather than changes to the hardware of the sensing array;

(c) relatively simple signal processing is required, thus facilitating high speed searching for specific plants.

Numerous variations and modifications will suggest themselves to persons skilled in the relevant arts, in addition to those already described, without departing from the basic inventive concepts. For example, the number of different wavelengths of sensors may be more than the two described in the preferred embodiments; more than two rings may be used in the concentric ring configuration of the sensors; the sensor array may also employ a geometric configuration of sensors, and is not limited to the simple linear array of the described embodiment. All such variations and modifications are to be considered within the scope of the present invention, the nature of which is to be determined from the forgoing description.

The invention claimed is:

1. An apparatus for selectively discriminating vegetation or plant matter, the apparatus comprising:
    light emitter for generating a beam of light that can be directed onto plants or plant matter over which the light emitter moves relative to the plants or plant matter;
    light sensor for sensing light transmitted from said light emitter and reflected from said plants or plant matter, and generating a reflection signal in response to said sensing;
    distance sensor arranged to measure the relative distance moved by said light emitter in relation to said plants or plant matter and further arranged to generate a distance signal in response to said measurement; and,
    processor operatively connected to said light sensor and distance sensor for combining said reflection signal and distance signal whereby, in use, different types of plants or plant matter can be discriminated.

2. An apparatus according to claim 1, wherein the processor combines the reflection signal and distance signal to determine the size and/or shape of the plant or plant matter.

3. An apparatus according to claim 1, wherein said distance sensor includes a wheel encoder for sensing the speed at which a vehicle on which the apparatus is mounted is moving over the ground.

4. An apparatus according to claim 3, wherein said wheel encoder generates a signal in the form of a train of pulses or pulse count, wherein the frequency of the pulses is directly proportional to the speed at which the vehicle moves over the ground, as well as of the distance it has travelled.

5. An apparatus according to claim 3, wherein a separate wheel encoder is provided on each side of the vehicle, so that the processor is able to identify when the vehicle is turning and adjust the response accordingly.

6. An apparatus according to claim 1, wherein said light emitter comprises a plurality of artificial light sources, each light source being adapted to transmit a beam of light at different wavelengths, whereby, in use, the reflection signal at each wavelength is used by the processor in combination with the distance signal to discriminate plants or plant matter.

7. An apparatus according to claim 1, wherein the processor is programmed to combine the reflection signal and distance signal to discriminate one type of plant matter from another type of plant matter and/or one type of plant matter from non plant matter.

8. An apparatus according to claim 1, said light sensor comprising a plurality of sensor assemblies mounted in an array.

9. An apparatus according to claim 8, each sensor assembly comprising two or more sensors mounted in close proximity and each adapted to detect the reflected light at different wavelengths.

10. An apparatus according to claim 9, wherein the sensors employed are photodiodes.

11. An apparatus according to claim 9, wherein a first sensor in each assembly is adapted to generate a sensing signal when it detects reflected light having a wavelength peaking between 550 nm and 650 nm.

12. An apparatus according to claim 11, wherein a second sensor in each assembly is adapted to generate a sensing signal when it detects reflected light having a wavelength peaking between 850 nm and 950 nm.

13. An apparatus according to claim 9, wherein each sensor assembly includes one or more further sensors adapted to generate a sensing signal when each further sensor detects reflected light having a predetermined wavelength in the visible, near infra-red or infra red wave bands, wherein the processor is operatively connected to the further sensors and the sensing signals from the further sensors are used to discriminate plants or plant matter.

14. An apparatus according to claim 9, wherein two or more sensors are mounted concentrically in order to reduce the incidence of "false positive" spectral response.

15. An apparatus according to claim 1, wherein the processor is configured to produce an output signal when a target plant is identified or when an object that is not a target plant is identified.

16. An apparatus according to claim 15, wherein the apparatus includes a response means arranged to provide a response to the output signal.

17. An apparatus according to claim 16, wherein the response means is one or more of:
- a solenoid valve arranged to operate a means for spraying; or
- a valve arranged to operate a means for distributing a powder or particulate material; or
- a recorder for recording the presence and location of the target plant and/or object;
- a cutter for cutting material in response to identification of the target plant or object; or
- a cultivator.

18. A method for selectively discriminating vegetation, or plant matter, the method comprising the steps of:
- generating a beam of light that can be directed onto plants or plant matter over which a light emitter moves relative to the plant or plant matter;
- sensing light transmitted from said light emitter and reflected from said plants or plant matter, and generating a reflection signal in response to said sensing;
- sensing the distance moved relative to said plants or plant matter by said light emitter and generating a distance signal in response to said sensing; and,
- processing said reflection signal and distance signal to determine the spectral characteristics and size and/or shape of the plants or plant matter whereby, in use, different types of plants or plant matter, including weeds, can be discriminated.

19. A method according to claim 18, wherein the light is sensed by one or more sensor assemblies having one or more sensors.

20. A method according to claim 19, wherein the sensor assemblies travel over the ground and each of the sensors in the sensor assemblies continually senses light reflected upwards from the ground surface.

21. A method according to claim 19, wherein the plants or plant matter travel underneath the sensor assemblies and each of the sensors in the sensor assemblies continually sensed the light reflected upwards from the plants or plant matter travelling beneath.

22. A method according to claim 20, wherein when a first affirmative spectral response signal occurs, the processor begins to "strobe" the sensor assemblies so that they only operate to sense the presence or absence of plant matter at discretely spaced intervals.

23. A method according to claim 22, wherein readings from each of a plurality of sensor assemblies used for sensing the reflected light are taken at uniformly spaced intervals over the ground surface, and are typically triggered by pulses generated via a wheel encoder used for sensing the distance travelled over the plants.

24. A method according to claim 23, wherein the interval spacing is set at a fixed distance, typically between 0.2 mm and 2 mm when travelling in a straight line.

* * * * *